(12) United States Patent
Young et al.

(10) Patent No.: US 6,208,885 B1
(45) Date of Patent: Mar. 27, 2001

(54) INJECTOR FOR INJECTION OF PRE-POLARISED FLUID INTO A PATIENT FOR MAGNETIC RESONANCE (MR) MEASUREMENT

(75) Inventors: Ian Robert Young, West Overton NR Marlborough; Joseph Vilmos Hajnal, London; Alasdair Stewart Hall, Northwood, all of (GB)

(73) Assignee: Picker International, Inc., Cleveland, OH (US)

( * ) Notice: Subject to any disclaimer, the term of this patent is extended or adjusted under 35 U.S.C. 154(b) by 0 days.

(21) Appl. No.: 09/224,790

(22) Filed: Jan. 4, 1999

(30) Foreign Application Priority Data

Jan. 27, 1998 (GB) .................................................. 9801664

(51) Int. Cl.⁷ ...................................................... A61B 5/05
(52) U.S. Cl. ............................................................ 600/420
(58) Field of Search .................................. 600/407, 409, 600/410, 411, 419, 420

(56) References Cited

U.S. PATENT DOCUMENTS

| | | |
|---|---|---|
| 4,335,835 | 6/1982 | Beigler et al. . |
| 4,450,079 | 5/1984 | Farr . |
| 5,427,104 | 6/1995 | Briend et al. . |
| 5,479,925 | 1/1996 | Dumoulin et al. . |
| 5,611,340 | 3/1997 | Souza et al. . |
| 5,617,859 * | 4/1997 | Souza et al. ........................ 600/420 |
| 5,626,137 | 5/1997 | Dumoulin et al. . |

FOREIGN PATENT DOCUMENTS 2 226 145    11/1974   (FR) .

* cited by examiner

*Primary Examiner*—George Manuel
(74) *Attorney, Agent, or Firm*—Timothy B. Gurin; John J. Fry; Eugene E. Clair

(57) ABSTRACT

A patient bed (1) of an MR imaging apparatus is provided with a tube (17) through which pre-polarised fluid can be injected into a patient in order to improve contrast when imaging veins, arteries or other vessels in the body. Fluid is delivered from pump (2) into a high field polarising magnet (3) and along a tube (4) to the patient. Valve (5) is provided so that fluid in the tube (4) downstream of the pre-polarised fluid can be discarded rather than being injected in the patient, and is associated with a reservoir into which the fluid to be discarded and the pre-polarised fluid can be rapidly injected. Then, when the pre-polarised fluid is injected into the patient, its magnetisation has not deteriorated by as much as it would have done if the tube (4) had been directly connected into the patient.

26 Claims, 1 Drawing Sheet

US 6,208,885 B1

INJECTOR FOR INJECTION OF PRE-POLARISED FLUID INTO A PATIENT FOR MAGNETIC RESONANCE (MR) MEASUREMENT

BACKGROUND OF THE INVENTION

This invention relates to injectors for injection of pre-polarised fluid into patients for magnetic resonance (MR) measurements.

As is well known, in MR imaging or spectroscopy measurements, a magnetic field is applied to a region of interest of the subject which causes nuclei with magnetic moments to align along the direction of the magnetic field, so that the region of interest acquires a net magnetisation parallel to the field. Application of an r.f. electromagnetic pulse of an appropriate frequency (the Larmor frequency) by way of a transmit coil in a direction orthogonal to the direction of the magnetic field excites the nuclei to resonance, thereby orienting the net magnetisation vector out of alignment with the main magnetic field. The subsequent r.f. relaxation signal which can be detected by a receive coil, generated by the nuclei as their return to their equilibrium condition in alignment with the main magnetic field, enables information about the material in question to be ascertained. To produce an image, coils are provided to vary the strength, but not the direction of the main magnetic field, in order to spatially encode the relaxation signals.

It is sometimes desired to produce an image e.g. of tissue of a patient, which gives prominence to vessels e.g. blood vessels, and the flow of blood is utilised to achieve this. In one method, the so-called "time-of-flight" method, a relatively short repetition time between successive r.f. excitation pulses is selected. Each r.f. pulse flips the longitudinal component of the net magnetisation out of alignment with the main magnetic field, and the longitudinal component then starts to recover to its original value. Since the repetition time is short, the longitudinal component does not have time to recover fully before the next and subsequent r.f. pulses, and achieves a steady state value considerably less than the undisturbed value. As far as blood entering a vessel is concerned, however, this has not been subjected to any r.f. pulses because these are specific to the region (usually a slice) being imaged. The longitudinal component of magnetisation of the moving blood is then undiminished by the saturation effect described for stationary tissue. Hence a larger signal is produced as the previously unexcited blood receives an excitation pulse within the imaged slice. As an alternative to the so-called time-of-flight methods described, phase contrasts methods have been used. A reference image of stationary nuclei is subtracted from an image of stationary nuclei and nuclei moving at a particular velocity, obtained by applying a gradient and inducing a phase shift of values appropriate to that velocity.

However, in both of these methods, the signal-to-noise ratio of the MR signal is improved if the main magnetic field is increased. This can be done, but implies the use of a larger, more expensive magnet.

A proposal has been made (U.S. Pat. No. 5,479,925, U.S. Pat. No. 5,626,137, U.S. Pat. No. 5,611,340, U.S. Pat. No. 5,617,859) to inject a pre-polarised fluid into a catheter inserted into the region of interest of a patient prior to MR imaging. A separate high power magnet has to be provided to pre-polarise the fluid, but this is much cheaper than making a corresponding increase in the strength of the main MR imaging magnet, since the latter has to provide a very homogeneous field, whereas the former does not. The pre-polarised fluid e.g. saline then produces a significantly increased signal in the vessels into which the catheter feeds. Clearly, the transfer and delivery must be achieved on a time scale that is short or comparable to the T1 relaxation time (relating to the time of decay of longitudinal magnetisation of the nuclei) or otherwise the stored magnetism will decay so much that little net signal enhancement will be detected.

The pre-polarising magnet must be housed at some distance from the main imaging magnet, or stray fields from the pre-polarising magnet will affect the homogeneity of the field of the imaging magnet.

There are two problems. Firstly, the rate of flow down the tube is limited by safety considerations. A faster flow would risk damaging any blood vessels. A flow of 5–9 ml/sec is the maximum feasible for veins, and this places a limit on the minimum transmit time from the large pre-polarising field to the MR scanner used to image the patient. Secondly, all the fluid in the tube that is between the pre-polarising field and the MR scanner must be pushed into the blood vessel before the pre-polarised material arrives.

SUMMARY OF THE INVENTION

The invention provides an injector for injection of pre-polarised fluid into a patient for MR measurements, comprising a dispenser for delivering a pre-polarised fluid along a tube to be connected to a catheter inserted into a patient, and a valve in the tube arranged to enable fluid in the tube ahead of the pre-polarised fluid to be discarded.

The provision of the valve reduces discomfort for the patient because only the polarised fluid is now injected.

Advantageously, the valve is capable of diverting the flow from a first reservoir to a second reservoir. Thus, the first reservoir can receive the unpolarised fluid, and the second reservoir can receive only the pre-polarised fluid. The contents of the latter can then be injected into the patient. This gives the possibility of significantly faster injection into the patient, because the dispenser can operate at a significantly greater pressure than would be possible for direct delivery into a vein, and the actual injection into the patient from the second reservoir can in fact be slower than would be possible if the dispenser injected directly into the vein.

BRIEF DESCRIPTION OF THE DRAWINGS

An injector for injection of pre-polarised fluid into a patient for MR measurements, constructed in accordance with the invention, will now be described by way of example with reference to the accompanying drawings, in which.

DETAILED DESCRIPTION

Figure 1:
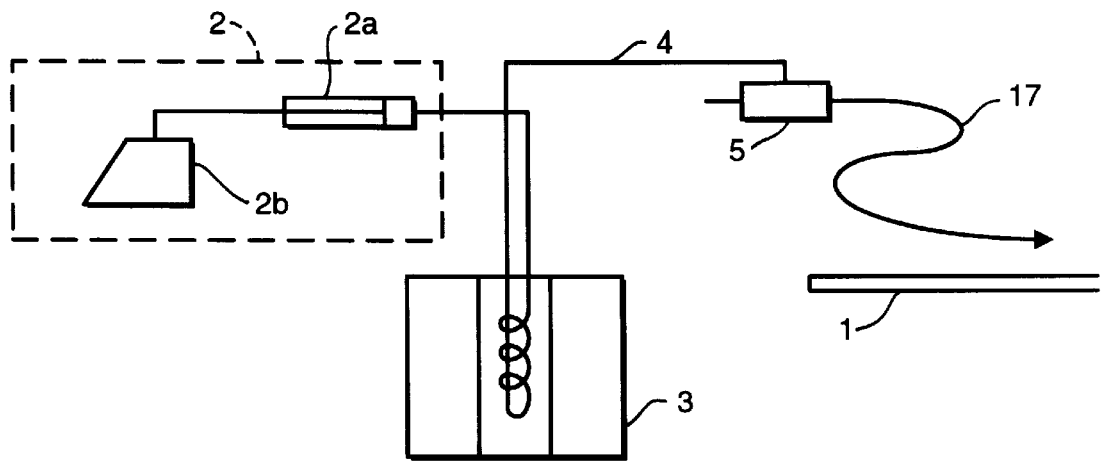
FIG. 1 shows the overall scheme of the injector diagrammatically.

A magnetic resonance (MR) imaging apparatus (not shown) has a bed 1 for a patient. The MR imaging apparatus has, as is well known, a main magnet for aligning the nuclei having magnetic moments with its field, gradient coils for spatially varying the magnitude but not direction of the magnetic field, in order to spatially code the MR signals, a transmit coil for transmitting an r.f. excitation pulse to a region of interest and a receive coil for detecting the MR signals which arise after the r.f. excitation pulse has been applied.

The MR imaging apparatus is designed to image particularly blood vessels. Because of problems outlined earlier, an improved signal-to-noise ratio is attainable if pre-polarised fluid e.g. saline is injected into the vessels before the MR image is captured.

Accordingly, a dispenser in the form of a pump 2 pumps saline through a high field polarising magnet 3 along a tube 4 for ultimate injection into the patient. The pump 2 includes a power injector 2a and a reservoir and control unit 2b.

The magnet 3 desirably has very high field, and active shielding to minimise the distance between the magnet 3 and the main magnet (not shown). Iron shielding is however feasible. There is no great need for homogeneity. In one example, the field of the magnet 3 was 7.0 Tesla, but a field of at least 10.0 T or even 15.0 T would be an advantage. One example of a suitable magnet had a warm bore of 55 mm diameter.

In accordance with the invention, a valve 5 is provided which enables fluid in the tube 4 ahead of the pre-polarised fluid to be discarded. In fact, the tube 4 will need to be relatively long, for example, 4–5 meters, because the high field polarising magnet 3 will inevitably have stray fields, and any disturbance of the field of the main imaging magnet will cause inaccuracies of the image produced by the MR imaging apparatus.

Figure 2:
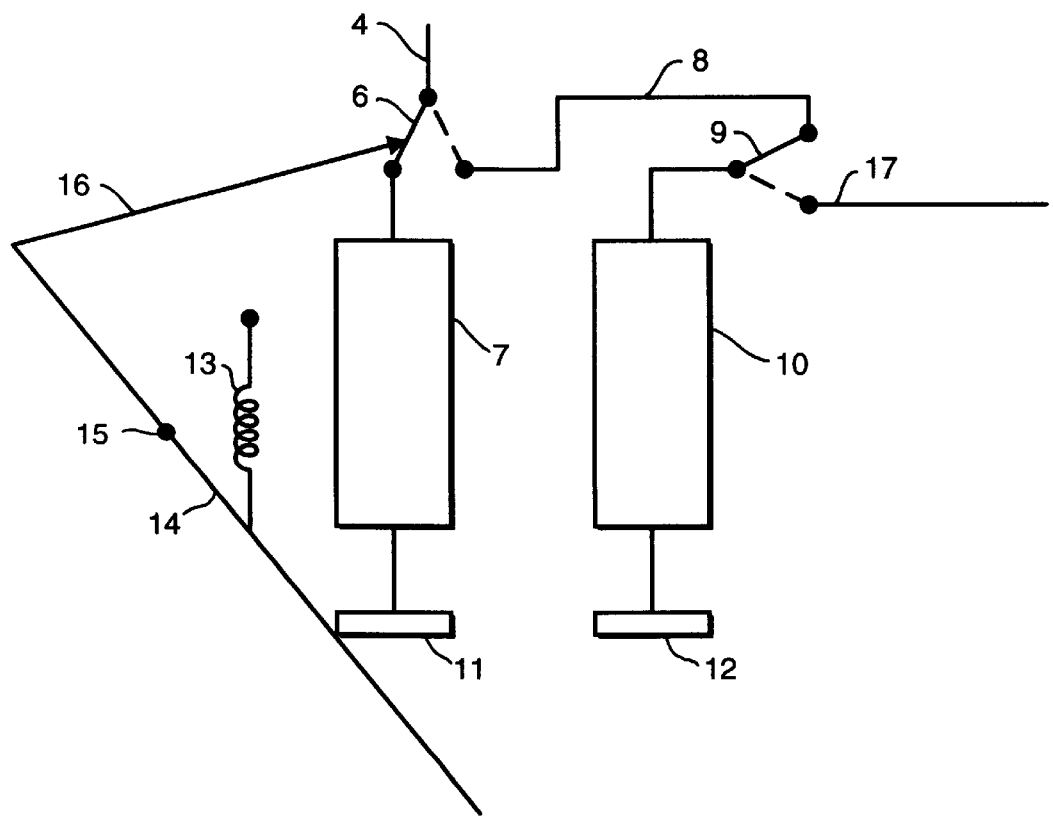
FIG. 2 shows the valve control of the injector, also diagrammatically.

Referring to FIG. 2, the valve 5 is shown in more detail. The valve includes a switch 6 which can either direct flow from the tube 4 into a first reservoir 7, or can divert it via an interconnecting pipe 8 and a switch 9 into a second reservoir 10. As the reservoirs 7 and 10 become filled, their plungers, 11, 12 are depressed (as seen in the drawing).

When plunger 11 of reservoir 7 is depressed, this acts on lever 14 which is pivoted at point 15 against the loading of a spring 13, and when the reservoir 7 has received a sufficient volume, linkage 16 operates the switch 6 to direct further flow to the second reservoir 10.

In operation, saline is pumped from the injector 2a of the pump 2 along pipe 4 into the pre-polarising magnet and into the valve 5. Typically the volume of the tube 4 within the magnet 3 could be around 20 ml and the volume of the tube 4 up to the valve 5 could be 40 ml. Consequently the switch 6 directs the first 40 ml of fluid into the reservoir 7, at which point the switch 6 is operated and the remaining 20 ml is then directed into reservoir 10. This can all take place at a very high speed. The pump 2 may be operating at 150 psi, which would be greatly in excess of what a vein could tolerate.

This is very important because the transfer and delivery of the fluid must be achieved on a timescale that is short or comparable to the T1 of the fluid, and the use of the pump enables transmit times that are perhaps ten times shorter than would be possible if direct injection to the patient was used. Of course, very little non pre-polarised fluid also enters the patient, which is significant in terms of comfort for the patient.

When the reservoir 10 has received the pre-polarised saline, that is, the volume of saline that was within the pre-polarising magnet, switch 9 is operated and the plunger 12 pushed in the reverse direction to inject the pre-polarised fluid along the tube 17 to a catheter in the patient. In the embodiment shown in FIG. 2, the plunger 12 is depressed by the force of the pre-polarised fluid entering, and then is expelled from the reservoir by operation of the plunger in the reverse direction. This could be done manually, in order to have the maximum control over the substance injected into the patient for safety reasons, but automatic operation would also be possible.

The MR imaging measurements are then made.

Reservoir 7 is reset by expelling its contents 7 when the switch is diverting flow to the second reservoir. The contents can be expelled to a suitable drain by means which are not shown. The plunger 11 will then be returned to an inward position ready for receipt of a volume from the pump the next time the injector is operated.

Variations may be made from the described embodiment without departing from the scope of the invention. Thus, while the injector has been described as being suitable for injecting into a vein, it could equally well be injected into an artery or into another vessel in the human body. Saline is a convenient fluid for the cardiovascular system, but other fluids e.g. blood could be used, and a gaseous fluid could even be used for injection into the lungs. Solutions containing phosphorus or carbon metabolites (the latter with, preferably, enhanced $C^{13}$ concentrations) could be used. Water would be suitable for the genito-urinary system. While the above embodiment relates to MR imaging, the invention would be equally beneficial if MR spectroscopy measurements were being made.

While a particular feature of the invention may have been described above with respect to only one of the illustrated embodiments, such features may be combined with one or more other features of other embodiments, as may be desired and advantageous for any given particular application.

From the above description of the invention, those skilled in the art will perceive improvements, changes and modification. Such improvements, changes and modification within the skill of the art are intended to be covered by the appended claims.

Having described a preferred embodiment of the invention, the following is claimed:

1. An injector for injection of pre-polarised fluid into a patient for MR measurements, the injector comprising:
   a dispenser for delivering pre-polarised fluid along a tube adapted to be connected to a catheter inserted into a patient; and
   a valve operatively connected to the tube and arranged to enable fluid in the tube ahead of the pre-polarised fluid to be discarded.

2. The injector of claim 1, wherein the valve includes a first position capable of diverting flow from a first reservoir to a second reservoir.

3. The injector of claim 2, wherein there is a switch associated with the second reservoir adapted to enable the contents of the second reservoir to be injected into the patient.

4. The injector of claim 2, including means associated with the first reservoir adapted to enable the contents to be discarded.

5. The injector of claim 2, wherein the valve is operated in response to the first reservoir receiving a predetermined quantity of fluid.

6. The injector of claim 1 wherein the fluid is gaseous.

7. A method for injecting pre-polarised fluid into a patient for MR imaging, the method comprising the steps of:
   supplying a fluid to a polarising apparatus;
   using the polarising apparatus to polarise the fluid;
   delivering the polarised fluid to a reservoir at a first delivery rate; and
   delivering the polarised fluid from the reservoir to a patient at a second delivery rate different than the first delivery rate.

8. The method of claim 7 further including the step of discarding a portion of the fluid prior to the step of delivering the fluid to the reservoir.

9. The method of claim 8 wherein the discarded portion of fluid has a lesser level of polarisation than the retained portion of fluid.

10. The method of claim 7 wherein the fluid is gaseous.

11. The method of claim 7 wherein the total delivery time between the polarising step and the step of delivering the polarised fluid to the patient is less than a predetermined duration of time that is functionally related to a relaxation time of the fluid.

12. The method of claim 11 wherein the relaxation time is the T1 relaxation time of the fluid.

13. The method of claim 7 wherein the polarised fluid is delivered to the reservoir through a tube.

14. The method of claim 7 further comprising the step of storing the polarised fluid in the reservoir.

15. A system for injecting pre-polarised fluid into a patient for MR imaging, the system comprising:
    a fluid supply;
    a polarizing means in fluid communication with the fluid supply;
    a first reservoir for receiving fluid;
    a valve in fluid communication with each of the polarising means and the first reservoir, whereby the valve is adapted to selectively discard fluid or direct fluid into the first reservoir; and
    a tube in fluid communication with the first reservoir for supplying polarised fluid to the patient.

16. The system of claim 15 wherein the fluid supply provides fluid at a first rate to the first reservoir and fluid is supplied to the patient at a second rate different than the first rate.

17. The system of claim 16 wherein the delivery time of the polarised fluid from the polarising means to the patient is less than a predetermined duration of time that is functionally related to a relaxation time of the fluid.

18. The system of claim 17 wherein the relaxation time is the T1 relaxation time of the fluid.

19. The system of claim 15 further including a second reservoir in fluid communication with the valve assembly, the second reservoir for receiving the discarded fluid.

20. The system of claim 15 wherein the fluid is gaseous.

21. A method of injecting pre-polarised fluid into a patient for MR imaging, the method comprising the steps of:
    supplying a polarised fluid from an associated polarising apparatus disposed at a first location;
    delivering the fluid to a second location nearer to the patient than the first location;
    delivering the polarised fluid from the second location to the patient.

22. The method of claim 21 further comprising the step of storing the polarised fluid at the second location.

23. The method of claim 21 wherein the step of delivering the fluid to the second location includes discarding a portion of the fluid.

24. The method of claim 21 wherein the polarised fluid has a first level of polarisation at the first location and a second level of polarisation when delivered to the patient that is (i) different than the first level of polarisation and (ii) greater than a predetermined level of polarisation.

25. The method of claim 21 wherein the fluid is gaseous.

26. The method of claim 21 wherein the polarised fluid is delivered to the second location through an associated tube.

* * * * *